United States Patent [19]

Deluhery et al.

[11] Patent Number: 4,705,044

[45] Date of Patent: Nov. 10, 1987

[54] DEFIBRILLATOR PADDLE

[75] Inventors: James G. Deluhery, Madison; Peter G. Truitt, Milton, both of Wis.

[73] Assignee: Kone Instruments Inc., Milton, Wis.

[21] Appl. No.: 796,810

[22] Filed: Nov. 12, 1985

[51] Int. Cl.[4] .......................... A61N 1/04; A61N 1/36; H05G 1/00

[52] U.S. Cl. .............................. 128/419 D; 128/419 S; 128/800

[58] Field of Search ................ 128/419 D, 419 S, 800

[56] References Cited

U.S. PATENT DOCUMENTS

| D. 244,153 | 4/1977 | Jones | 128/419 D |
|---|---|---|---|
| D. 252,821 | 9/1979 | Moore et al. | 128/419 D |
| 3,670,736 | 6/1972 | Panico | 128/419 D |
| 3,702,613 | 11/1972 | Panico et al. | 128/419 D |
| 3,762,420 | 10/1973 | Moore et al. | 128/419 D |
| 3,961,623 | 6/1976 | Milani et al. | 128/419 D |
| 4,097,113 | 6/1978 | McKelvy | 128/419 D |

Primary Examiner—William E. Kamm
Attorney, Agent, or Firm—Mason, Kolehmainen, Rathburn & Wyss

[57] ABSTRACT

A defibrillator paddle includes a pediatric electrode of relatively small size attached to a mounting portion of a housing having a handle. An adult electrode assembly is releasably mounted to the mounting portion of the housing by a quick release latch mechanism. The adult electrode assembly includes an adult electrode larger than the pediatric electrode. The pediatric electrode nests within the adult electrode assembly and a spring makes electrical contact between the electrodes when the adult electrode assembly is mounted.

5 Claims, 9 Drawing Figures

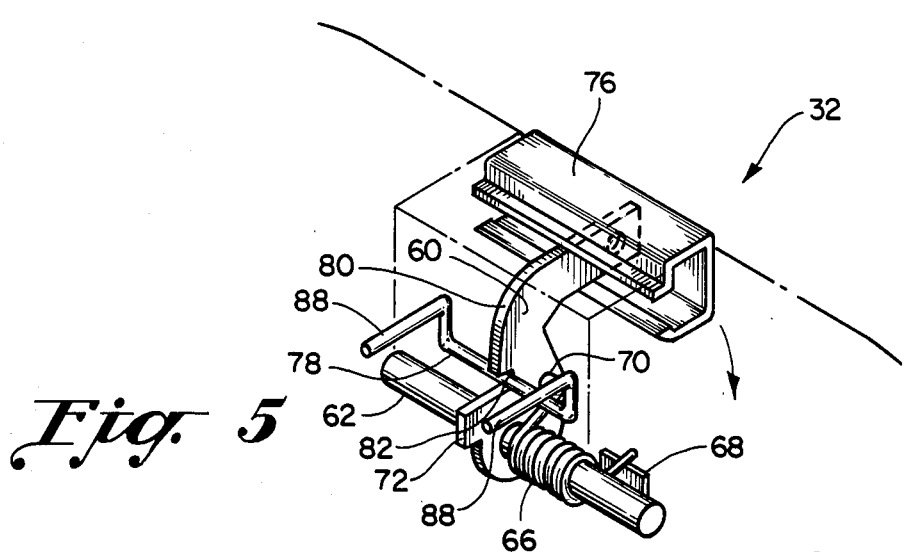
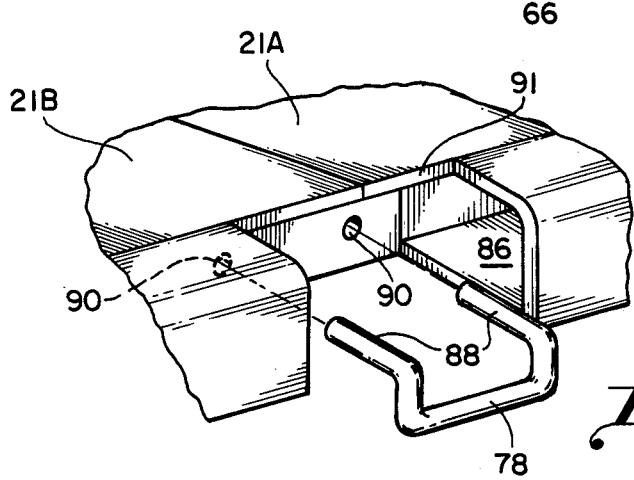
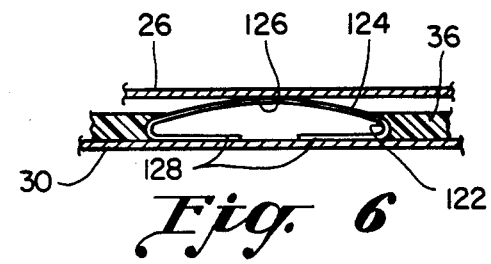
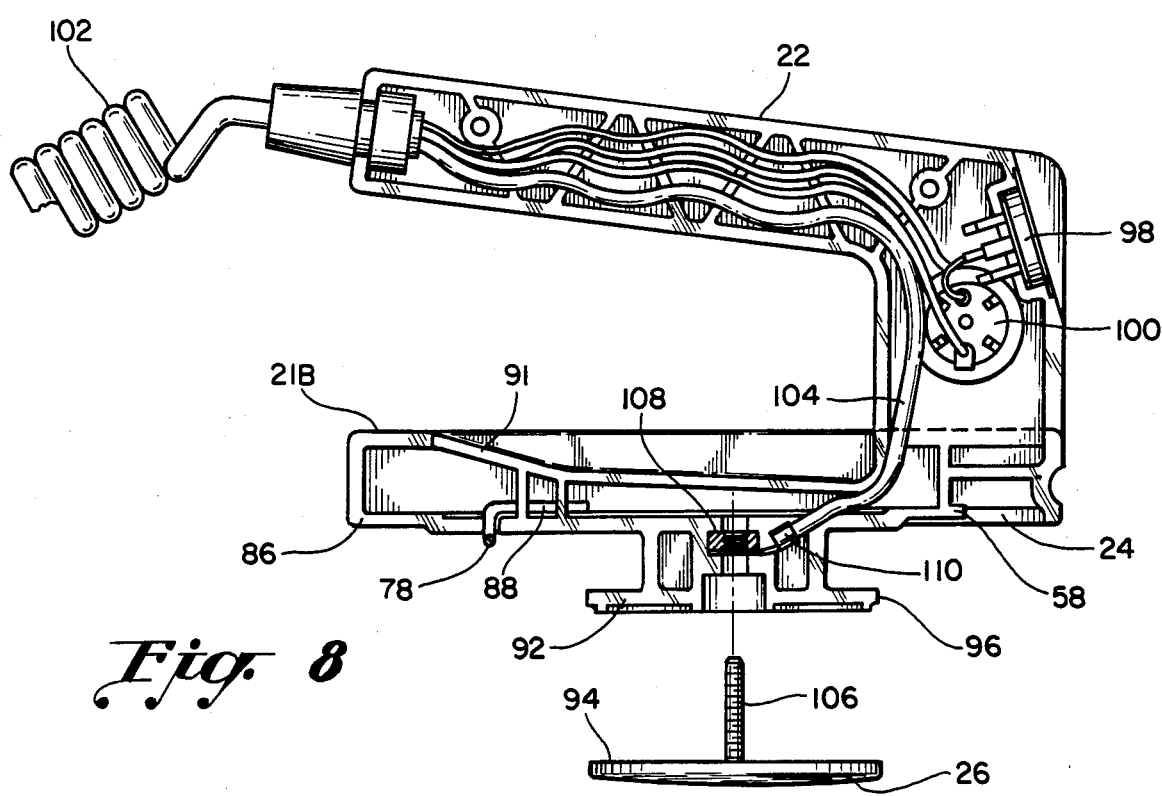

DEFIBRILLATOR PADDLE

The present invention relates to defibrillator paddles, and more particularly to a defibrillator paddle having both an adult electrode and a readily accessible pediatric electrode.

Defibrillators are used to halt cardiac fibrillation by the application of electrical shock to the chest of a patient so that a normal heartbeat may resume. Paddles connected to the defibrillator are held against the chest of a patient and a switch is operated to control the activation of the defibrillator. The paddle includes a handle grasped by the operator and an electrically conductive electrode placed into electrical contact with the patient.

Due to differences in physical size, different electrode configurations are required when defibrillators are used with adults and children. Defibrillators are typically supplied with paddles having adult electrodes, and these paddles are normally left connected to the defibrillator in a ready condition. However, the electrodes of these paddles are too large to be used in a pediatric cardiac emergency. Although smaller pediatric paddles with electrodes properly sized for children have been offered as optional equipment for defibrillators, use of the pediatric paddles requires that the adult paddles be disconnected and that the necessary pediatric paddles be located and connected before the defibrillator can be used. Due to the need for haste and other adverse conditions that often exist during a cardiac emergency, the necessity for using different paddles with the defibrillator is not desirable. Since defibrillators are employed under crisis conditions, such as by medical or paramedic personnel during a hospital or ambulance emergency, it is of the utmost importance that the defibrillator and associated equipment be easy to use, reliable and sturdy.

An important object of the present invention is to provide a paddle for defibrillators capable of use with both adults and children without the necessity for locating and connecting different components to the defibrillator. Other important objects are to provide a defibrillator paddle having both adult and pediatric electrodes readily accessible and easy to use under emergency conditions, to provide a paddle overcoming the problem of unavailability or loss of pediatric paddles when a pediatric cardiac emergency is encountered, to provide a paddle which is sturdy, reliable and easy to use, and to provide a paddle for defibrillators which overcomes the disadvantages of paddles having single electrodes of the type used in the past.

In brief, in accordance with the above and other objects of the present invention there is provided a defibrillator paddle having a housing including a handle and a mounting portion. An electrically conductive pediatric electrode is attached to the mounting portion at a location spaced from the handle. A switch carried by the housing controls the application of a defibrillator shock signal to the pediatric electrode. An adult electrode assembly is releasably attached to the mounting portion of the housing, and includes an electrode base and an adult electrode attached to the base. The adult electrode has a surface area larger than the surface area of the pediatric electrode, and the pediatric electrode is nested within the adult electrode assembly in the assembled condition. A contact carried by the adult electrode assembly interconnects the pediatric and adult electrodes when the adult electrode assembly is connected to the mounting portion. A quick release system permits the adult electrode assembly readily to be detached to expose the pediatric electrode when required and permits the adult electrode assembly easily to be attached for normal use.

The present invention together with the above and other objects and advantages may be best understood in connection with the following detailed description of the preferred embodiment of the invention illustrated in the accompanying drawings, wherein:

FIG. 5 is an enlarged perspective view of the quick release latch assembly indicated by line 5—5 of FIG. 4 and of the quick release catch;

FIG. 6 is an enlarged sectional view taken along the lines 6—6 of FIG. 4 showing the spring contact of the adult electrode assembly;

FIG. 7 is an enlarged perspective view showing a portion of the defibrillator paddle housing and the quick release catch in unassembled condition;

FIG. 8 is a side view of half of the defibrillator paddle housing with the pediatric electrode in an unassembled condition.

Figure 1:
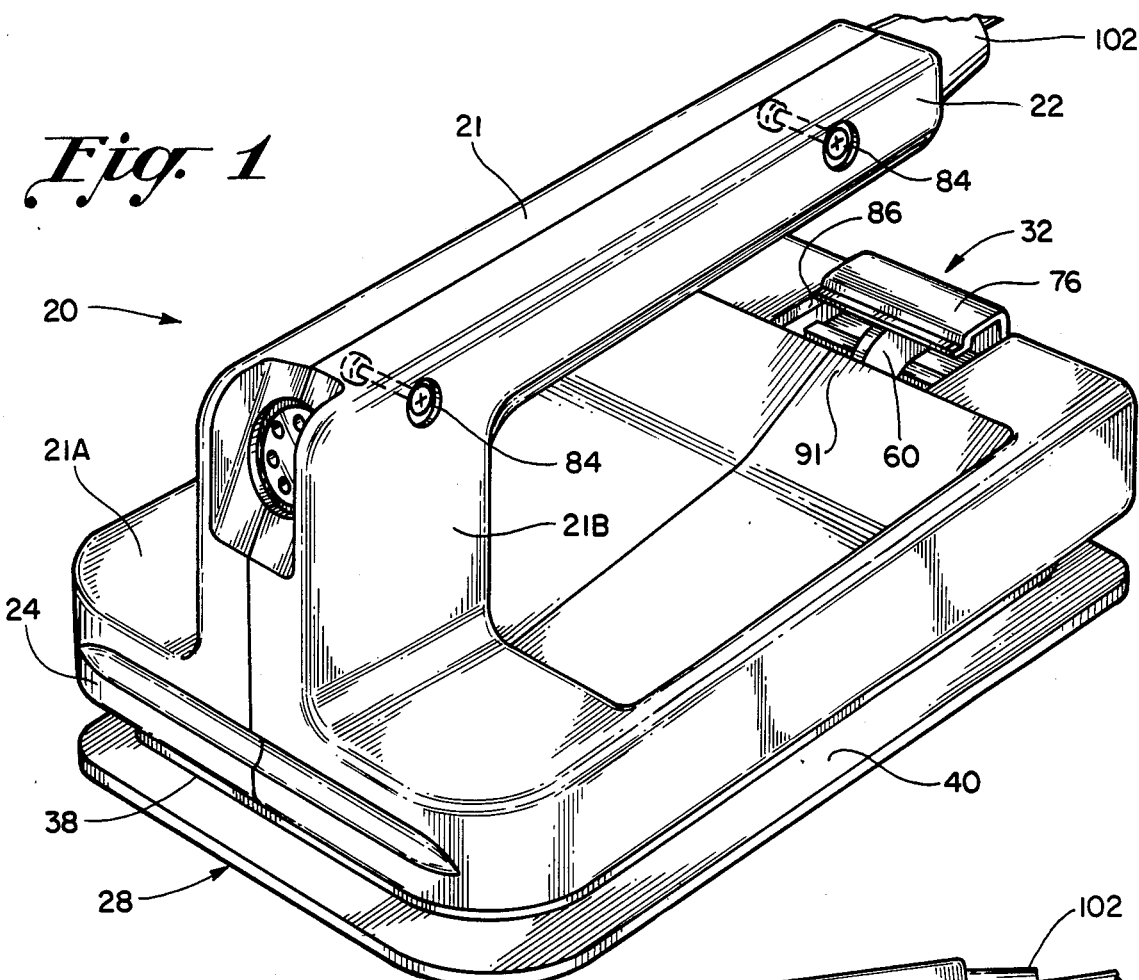
FIG. 1 is a perspective view of a defibrillator paddle constructed in accordance with the present invention.
Figure 2:
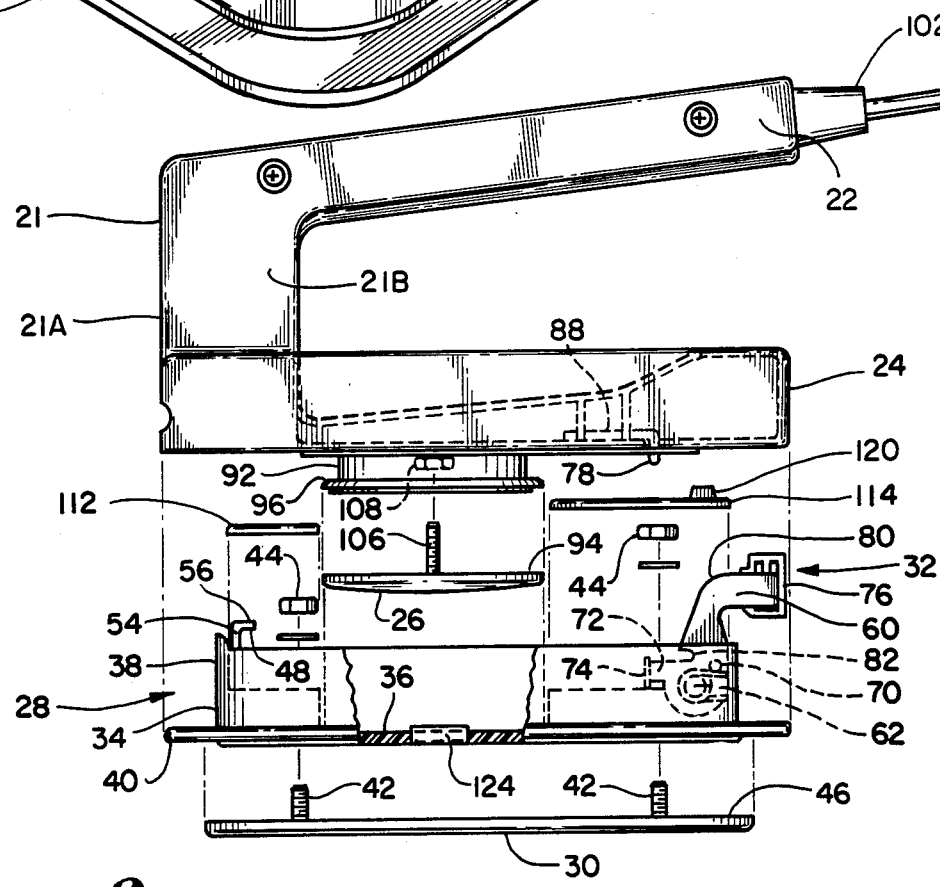
FIG. 2 is an exploded side view on a reduced scale showing components of the defibrillator paddle in unassembled condition.
Figure 9:
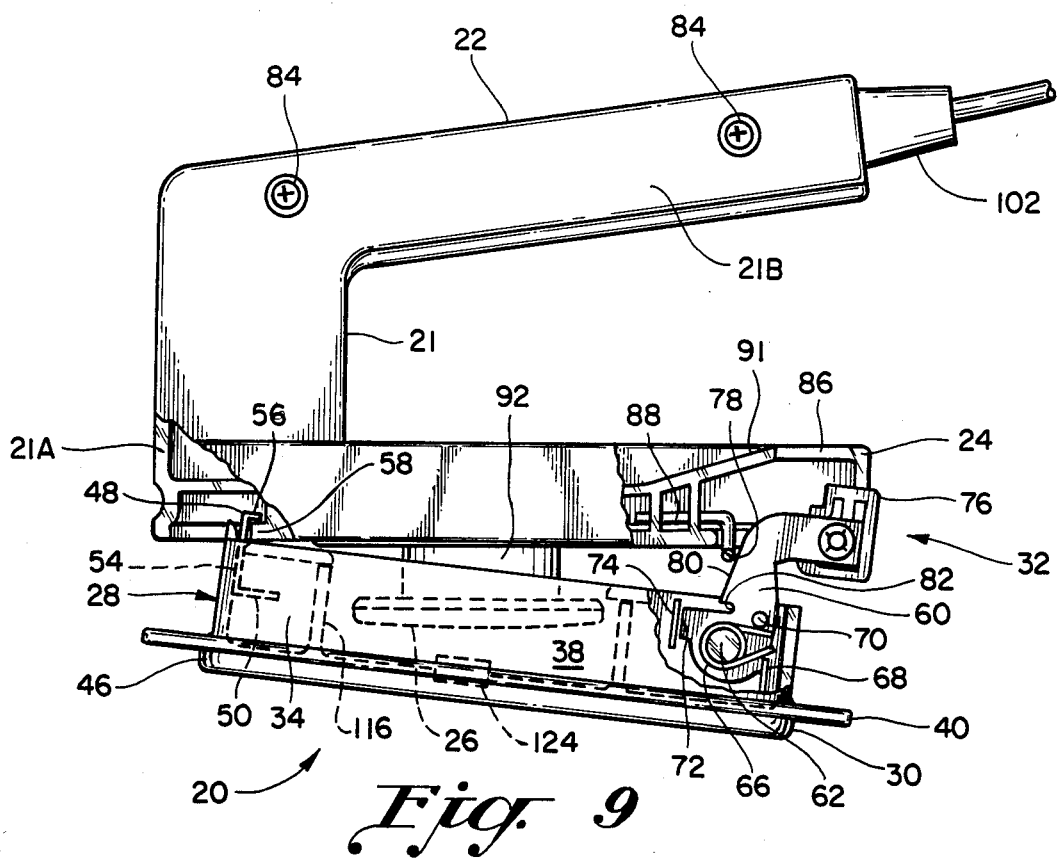
FIG. 9 is a side view, with portions broken away, showing the defibrillator paddle with the adult electrode assembly partially assembled.

Having reference now to the drawings and initially to FIGS. 1 and 9, there is illustrated a defibrillator paddle designated as a whole by the reference numeral 20 and constructed in accordance with the principles of the present invention. Paddle 20 includes a housing 21 having a handle 22 and a mounting portion 24. In accordance with an important feature of the present invention, a pediatric electrode 26 of relatively small size is attached to the mounting portion 24 and normally is nested within an adult electrode assembly generally designated as 28. The adult electrode assembly 28 includes an adult electrode 30 larger than the pediatric electrode 26, and the assembly 28 is readily attached to or removed from the mounting portion 24 by means of a quick release mechanism generally designated as 32. Since the pediatric electrode 26 is permanently associated with the paddle 20 and normally nested within the adult elecrode assembly 28, either electrode is immediately available without the necessity for locating additional parts or changing the connections to a defibrillator.

Adult electrode assembly 28 includes a body 34 formed preferably by molding of an electrically insulating material such as a suitable plastic. Body 34 is generally rectangular in shape (FIG. 3) and includes a bottom wall 36 and a continuous upstanding side wall 38. A continuous flange 40 extends outwardly around the entire circumference of the body 34. As best seen in FIG. 1 the flange 40 is generally the same shape as the housing mounting portion to provide a trim appearance.

Adult electrode 30 is attached beneath the bottom wall 36. Elecrode 30 is also generally rectangular in shape and, for example, may be roughly 2.3 inches by 3.7 inches in size. Threaded studs 42 extend upwardly from the adult electrode 30 into recesses formed above bottom wall 36 (FIG. 4) and are engaged by nuts 44 to attach the electrode snugly over the bottom wall 36 with a flange 46 of the electrode 30 tight against the underside of the flange 40 of the body 34. Adult electrode 30 is made of an electrically conductive material such as stainless steel, and the flange 40 of body 34 extends outwardly beyond the periphery of the electrode as a protective shield.

Figure 3:
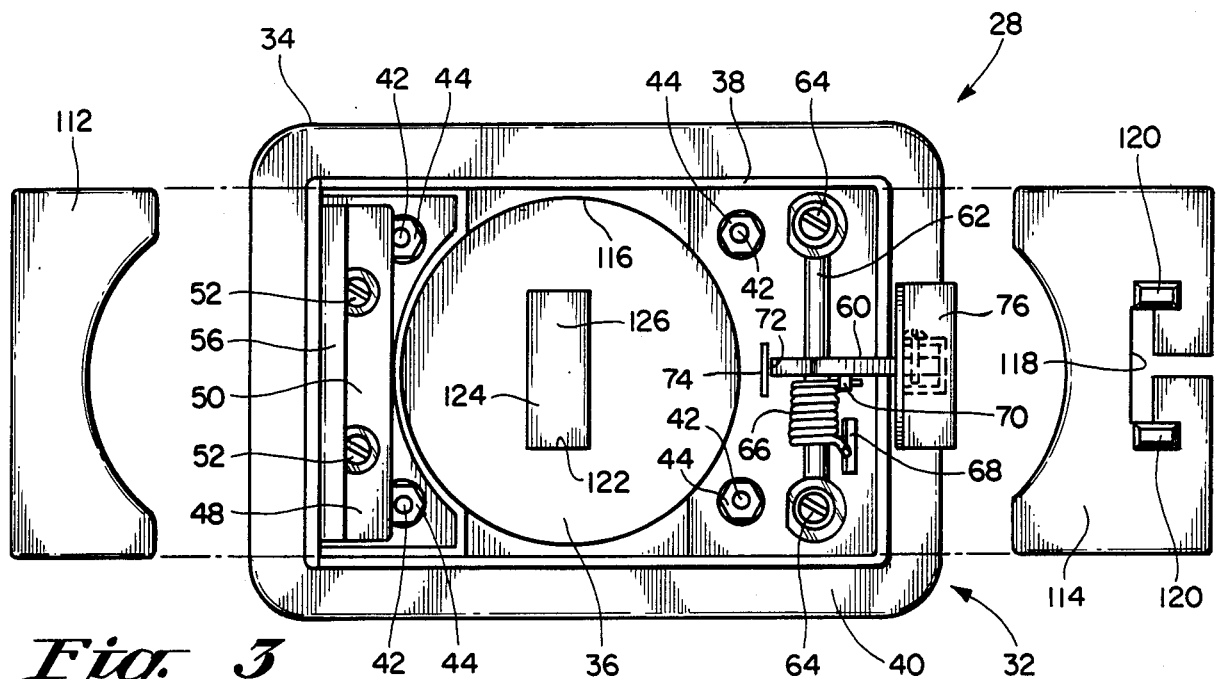
FIG. 3 is a top view of the adult electrode assembly of the defibrillator paddle with the covers shown in the unassembled condition.
Figure 4:
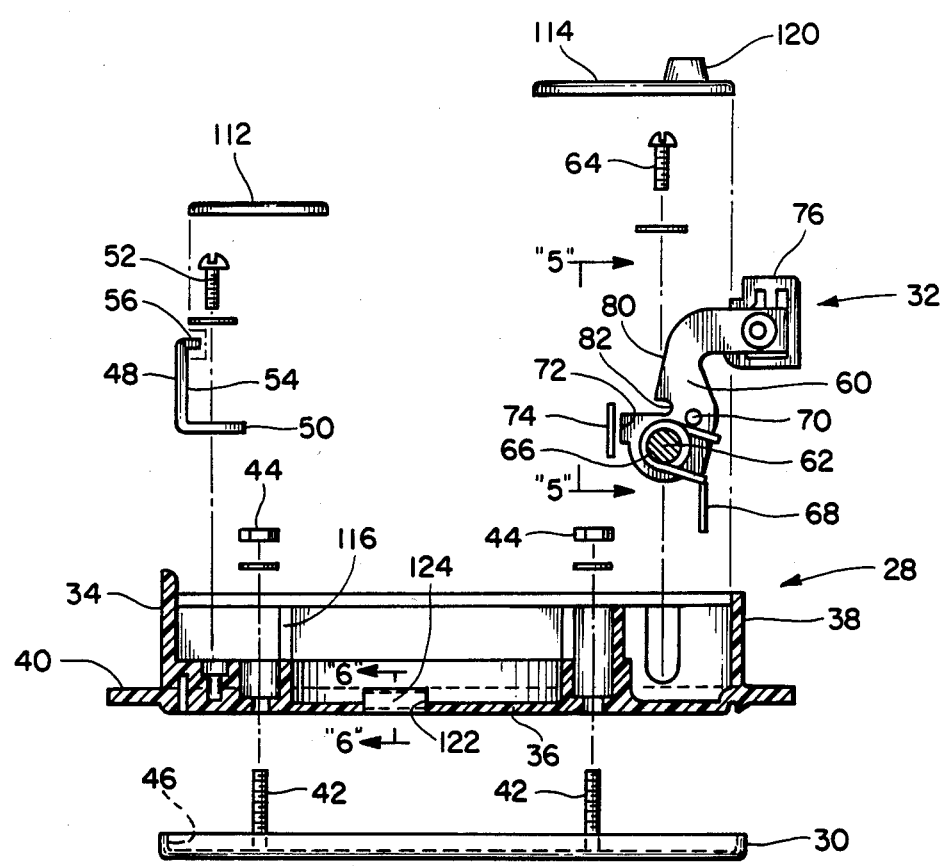
FIG. 4 is a side view, partly in section, showing the components of the adult electrode assembly in unassembled condition.

An elongated latch plate 48 cooperates with the quick release mechanism 32 in mounting the adult electrode assembly 28 to the paddle housing 21. A base portion 50 of plate 48 is held to a raised portion of the bottom wall 36 by a pair of screws 52 (FIGS. 3 and 4). Plate 48 includes an upstanding portion 54 received adjacent the sidewall 38 and terminating in an inwardly directed lip 56 engageable over a corresponding lip 58 of the paddle housing 21 (FIGS. 8 and 9).

Quick release mechanism 32 includes a latch lever 60 pivotally mounted on a pivot pin 62 held in a cradle structure defined above wall 36 (FIG. 4) by a pair of screws 64 and associated washers overlying the ends of the pin 62. A spring 66 surrounding pin 62 has ends engaged with a stop plate 68 held in the body 34 and with a projection 70 on the lever 60. The spring biases the lever to a latched position with an abutment 72 against a second stop plate 74 also held in body 34. Lever 60 is pivoted about pin 62 away from the latched position against the force of spring 66 by depressing a latch button 76 carried by the accessible outer end of the lever 60.

In order to mount the adult electrode assembly 28 onto the mounting portion 24 of the paddle housing 21, the lip 56 of latch plate 48 is first engaged over the lip 58 of housing 21 in the manner indicated in FIG. 9. Then the adult electrode assembly 28 is pivoted up against the mounting portion 24 to engage latch lever 60 with a catch 78 carried by the mounting portion 24. The catch first engages a cam surface 80 on lever 60 moving the lever away from the latched position. Then, as the adult electrode assembly 28 reaches its home position, the catch 78 seats in a latch recess 82 in lever 60. This mounting system has the advantage that it provides a very stable and firm attachment of the adult electrode assembly to the paddle by virtue of the elongated lips 56 and 58 cooperating with the essentially single point contact of the catch 78 and the recess 82. Moreover, the latching arrangement is essentially self guiding and very easy to use. The adult electrode assembly 28 is easily attached to the paddle in a minimum of time, and conversely is easily released simply by depressing the button 76 and pivoting the adult electrode assembly down while disengaging the lips 56 and 58.

Housing 21 of the paddle 20 is formed of two separate segments in the form of similar housing halves 21A and 21B. These are essentially mirror images of one another and are joined at a plane of separation generally coinciding with the vertical central longitudinal axis of the paddle 20. Housing halves 21A and 21B are preferably formed as by molding of an electrically insulating plastic material. The two halves 21A and 21B are held in assembled relation by a pair of screws 84 in the handle portion 22 and also by the catch 78 and the pediatric electrode 26.

The halves of the handle 21 cooperate in defining a recess 86 in which catch 78 is located and in which the quick release button 76 is received when the adult electrode assembly 28 is assembled (FIGS. 1 and 7). Catch 78 is a formed wire member having a pair of legs 88. When assembled to housing 21, the legs 88 are press fit into corresponding openings 90 one of which is formed in each housing half 21A and 21B. The catch 78 forms a dual purpose as part of the quick release mechanism 32 and as the device for holding together the rearward portions of the housing halves. A protective shelf 91 shields catch 78 to prevent contact with a user's hand. When the paddle 20 is assembled with the adult electrode assembly 28 in position, the quick release button 76 is easily accessible in the recess 86 (FIG. 1) and can rapidly be located by touch alone and depressed to remove the adult electrode assembly.

A circular boss 92 formed on the underside of the mounting portion 24 and spaced well away from the handle 22 receives the pediatric electrode 26. Electrode 26 is formed of an electrically conductive material such as stainless steel and may, for example, be about 1.9 inches in diameter. A continuous flange 94 is held tight against a mounting flange 96 of the boss 92 when the pediatric electrode 26 is assembled. Since the electrode 26 is substantially smaller than the mounting portion 24, the electrode 26 is protectively shielded when in use.

In accordance with known practice, the paddle 20 includes a trigger switch 98 disposed at the front of the handle 22 (FIG. 8). The paddle may also include a control switch 100 mounted to the housing half 21B and shown only in FIG. 8. An electrical cable 102 extends from the rear of the handle portion 22 and includes a connector (not shown) for connection to a cardiac defibrillator. Wires of the cable 102 extend within the handle 22 (FIG. 8) to the switch 98 and/or 100 so that the defibrillator may be triggered and/or controlled from the paddle 20. One wire 104 of cable 102 forms a signal path for a defibrillator shock signal applied from the cardiac defibrillator to the electrode 26.

A mounting stud 106 extends from the central axis of the circular pediatric electrode 26. A nut 108 is nonrotationally captured within boss 92 and between the housing halves 21A and 21B. Stud 106 is threaded into nut 108 by rotation of the pediatric electrode 26, and two different functions are accomplished in addition to attachment of the electrode 26 to the housing. First, as the stud 106 is threaded home, the flange 94 engages the bottom of the boss 92 to assist in firmly holding together the two halves 21A and 21B of the housing 21. Second, nut 108 is drawn tightly against the contact portion of an electrical terminal 110 crimped to the end of wire 104, thereby establishing an electrical connection of high current capacity between the cardiac defibrillator and the pediatric electrode 26.

When the adult electrode assembly 28 is assembled to the mounting portion 24 of the paddle housing 21, the pediatric electrode 26 carried on boss 92 is nested within the adult electrode assembly. A pair of covers 112 and 114 (FIGS. 3 and 4) are secured, for example by adhesive, to wall 38 and cover the upper portions of the adult electrode assembly 28 within the sidewall 38, but leave open a circular central nest 116. Cover 114 includes a T-shaped slot 118 for receiving the lever 60 and the catch 78, and a pair of projecting portions 120 serving as guides between the mounting portion 24 and the assembly 28.

Nest 116 is sized snugly to receive and protect the pediatric electrode 26 and includes provision for establishing a high current capability electrical connection between the pediatric and adult electrodes 26 and 30 when the adult electrode assembly 28 is mounted. As best seen in FIGS. 3 and 6, the bottom wall 36 of body 28 includes an opening 122 extending through the wall in which is captured an electrically conductive metal spring having a substantial length, for example, about one inch. When installed in the recess 122, the spring 124 assumes a shape with a bowed, upper contact portion 126 and a pair of lower leg contact portions 128. When the adult electrode assembly 28 is mounted with catch 78 seated in recess 82 of lever 60, the spring 124 is compressed firmly between the bottom surface of the pediatric electrode 26 and the top surface of the adult electrode 30. A large area electrical contact is achieved between each electrode and the spring 124 for effective transfer of defibrillator shock signals to the adult electrode 30. The spring 124 also prevents looseness and stabilizes the mounting of the adult electrode assembly 28 on the mounting portion 24.

While the invention has been described with reference to details of the preferred embodiment, it should be understood that such details are not intended to limit the scope of the invention as defined in the following claims.

What is claimed and desired to be secured by Letters Patent of the United States is:

1. A defibrillator paddle comprising in combination:
   a paddle housing including a handle and a mounting portion;
   an electrically conductive pediatric electrode attached to said mounting portion and spaced from said handle;
   electrical circuit means including switch means mounted on said housing for applying a defibrillator shock signal to said pediatric electrode;
   and an adult electrode assembly releasably attached in an assembled condition to said mounting portion;
   said adult electrode assembly including an electrode base and an adult electode attached to said base;
   said adult electrode having a surface area larger that the surface area of said pediatric electrode;
   said pediatric electrode being nested inside of said adult electrode assembly in said assembled condition;
   contact means carried by said adult electrode assembly for electrically connecting said pediatric electrode to said adult electrode in said assembled condition; and
   a quick release latch engageable between said adult electrode assembly and said paddle housing including first and second interlocking elements on said mounting portion and said electrode base and further including a catch and a resiliently movable latch spaced from said first and second elements on mounting portion and said electrode base;
   said latch including a lever mounted in said electrode base for pivotal movement and a spring for resiliently biasing said lever into engagement with said catch.

2. The defibrillator paddle of claim 1, said housing including two joined housing segments and said catch comprising a member attached to both said segments for assisting in holding them together.

3. The defibrillator paddle of claim 1, said pediatric electrode and said adult electrode being generally shaped as flat planar members and being generally parallel to one another and spaced apart in said assembled condition.

4. The defibrillator paddle of claim 6, said contact means comprising a resiliently compressible electrically conductive spring member sandwiched in compression between said electrodes in said assembled condition.

5. The defibrillator paddle of claim 1, said paddle housing including two joined housing segments, said pediatric electrode engaging both said housing segments for assisting in holding them together.

* * * * *